United States Patent [19]
Kitagawa et al.

[11] Patent Number: 4,629,862
[45] Date of Patent: Dec. 16, 1986

[54] SAMPLE HEATER FOR USE IN MICROSCOPES

[75] Inventors: Hisao Kitagawa; Yasuo Inoue; Tadafumi Fujihara; Itaru Endo; Yoshihiro Shimada, all of Hachioji, Japan

[73] Assignee: Olympus Optical Company Ltd., Japan

[21] Appl. No.: 671,732

[22] Filed: Nov. 15, 1984

[30] Foreign Application Priority Data

Mar. 28, 1984 [JP] Japan .............................. 59-44814[U]
Mar. 28, 1984 [JP] Japan .............................. 59-44815[U]
Mar. 29, 1984 [JP] Japan .............................. 59-45643[U]
Mar. 29, 1984 [JP] Japan .............................. 59-61770[U]
Apr. 2, 1984 [JP] Japan .............................. 59-48228[U]

[51] Int. Cl.⁴ .......................... H05B 3/22; G02B 21/30
[52] U.S. Cl. .................................... 219/200; 219/201; 219/385; 219/521; 350/533
[58] Field of Search .............. 219/200, 201, 385, 386, 219/387, 521, 219; 350/533

[56] References Cited

U.S. PATENT DOCUMENTS 2,995,643  8/1961  Gabler ................................. 219/201
3,472,726 10/1969  Scheidegger ....................... 350/533

FOREIGN PATENT DOCUMENTS 504783    8/1954  Canada ................................ 350/533
457990    3/1928  Fed. Rep. of Germany ...... 350/533
599600    7/1934  Fed. Rep. of Germany ...... 350/533
AS1284119 11/1968  Fed. Rep. of Germany .
1283558   11/1968  Fed. Rep. of Germany ...... 350/533
57-41774  of 1982  Japan .

OTHER PUBLICATIONS

Tynan, E. E. and R. J. von Gutfield, "Microscope Stage Sample...", IBM Tech. Disc. Bull., vol. 17, No. 8, Jan. 1975, pp. 2507–2508.
Sundquist, B. E., "High Temperature Microscope Stage", The Review of Scien. Instr., vol. 31, No. 4, Apr. 1960, pp. 425–427.
Hay, J. N., "A Thermostat Control Unit ...", J. Sci. Instrum., 1964, vol. 41, pp. 465–467.

Primary Examiner—E. A. Goldberg
Assistant Examiner—Teresa J. Walberg
Attorney, Agent, or Firm—Ostrolenk, Faber, Gerb & Soffen

[57] ABSTRACT

A heater for microscopes for heating a sample and maintaining the sample, which is mounted on a platform of the microscope, at a preset temperature during observation of the sample. The heater includes a platform for supporting thereon a sample container and a heater for heating at least part of the platform. A first heater box is fitted, open end down, over the platform and is connected thereto to form a first space which surrounds the sample container. A second heater box is then fitted over the first heater box in such a manner that a second space which surrounds the first heater box is formed. Heater means are provided for heating the second space. Accordingly, the temperatures in the first space and in the second space can be controlled independently to achieve better control over the temperature of the sample which is to be observed and to control condensation which may otherwise form in the sample holding container.

24 Claims, 27 Drawing Figures

SAMPLE HEATER FOR USE IN MICROSCOPES

BACKGROUND OF THE INVENTION

The present invention relates to a sample heater for use in microscopes, and more particularly, to a heater which is capable of heating a sample positioned on a microscope sample supporter to a preset temperature.

A conventional sample heater for use in a microscope has been disclosed in Japanese Utility Model Publication No. Sho 57/1982-41774 published on Sept. 13, 1982, for example.

In a conventional heater, air of a predetermined temperature is fed into a heater box using a fan to heat or cool a container which contains a sample and its vicinity, whereby the sample is kept at the predetermined temperature.

The conventional heater has, however, the following disadvantages.

(1) Since air is fed into the heater box using a fan, there is a possibility that extraneous dust will be blown onto the sample and that dust within the box will stick to the sample.

(2) When the heated air is fed into the heater box, an increased response time is required until the sample attains a predetermined temperature because of the low heat capacity of air. When the temperature of the sample is controlled in accordance with a time-program control an increased time is required for temperature stabilization.

(3) When an open type culture observation container is employed, vapor steam evaporated from culture fluid within the container sticks to the inner surface of the heater box to cloud the inner surface. This degrades the ability to observe the sample.

In addition, the conventional heater has a temperature sensor disposed adjacent to the sample but away from it so as not to obstruct the view from the microscope. Therefore, a temperature controller controls the sample to a temperature based on an output signal from the temperature sensor and not from the sample itself.

However, when cultured cells are observed with a microscope, a culture observation container which is generally employed, for example, is so large in size in comparison with the culture that even when a temperature sensor is arranged in close vicinity to the container a significant temperature difference exists the actual temperature and the measured temperature. Positioning the temperature sensor within the container in the vicinity of the observation position may allow entry of various germs into the container through the temperature sensor so that every measurement requires cleaning and sterilization of the temperature sensor.

Some conventional sample heaters have an arrangement in which a heater plate is mounted on the microscope's sample supporter and a culture observation container is mounted on the heater plate to keep the sample within the container in a fixed temperature by the direct heat conduction from the heater plate.

In such sample heaters, since the heater plate is mounted on the sample support platform, or rest platform as it will be referred to herein, the sample is raised by thickness of the heater plate. In addition, a comparatively small diameter of a through-hole for the observation in the heater plate is chosen in order to improve the thermal insulation effect in the vicinity of the optical axis so that an allowable upward movement of an objective lens of an inverted type microscope is insufficient for the purpose of focusing. As a result, an out of focus condition may be caused and especially with an objective lens of the high magnification its operational range is generally so reduced that the front end of the objective lens hits against the heater plate, making it impossible to attain a required operational range. Thus, the microscope is limited to an objective lens of the small magnification. Furthermore, when a culture observation container such as a laboratory dish, flask and microtest plate is used, the sample is further raised by the bottom thickness of the container and thus the foregoing problem becomes more acute. When a non-inverted type microscope is used, the same problem is caused in connection with condenser lens.

Recently plastic laboratory dishes or flasks have been used. Such a plastic container generally has an annular projection on its bottom outer peripheral edge, which serves as a leg in the form of bottom rim to maintain the flatness of the bottom surface and to prevent the bottom from being damaged. Accordingly, when a sample within a culture observation container such as a laboratory dish or flask made of plastic is maintained at a fixed temperature by heating at least part of a rest for a microscope or a heater plate mounted on the rest so as to heat the observation container mounted on the rest or the heater plate by the heat conduction, only the projection is in contact with the rest and an air layer forms between the rest and the container bottom, so that uniform temperature is not obtained in the container. Thus, the sample within the container will not be heated properly. Also, the air layer produces a low thermal efficiency and an increased response time.

SUMMARY OF THE INVENTION

It is an object of the present invention to provide a sample heater using a heater box which is impervious to dust created by a fan and which prevents dust within the heater box to be blown about and in which dust within the heater box to be blown about and in which temperature control response time is reduced. Even when an open type culture observation container is used the inner surface of the heater box is not clouded.

It is another object of the present invention to provide a sample heater for use in a microscope which permits an accurate temperature control of a sample to a predetermined value without affecting the sample arranged on the rest of the microscope.

It is a further object of the present invention to provide a sample heater for use in a microscope in which the effects of thickness of the heater plate are eliminated and which provides proper temperature control during static or variable temperature control conditions.

It is a still further object of the present invention to provide a sample heater for use in a microscope which has a uniform distribution of temperature, increased thermal efficiency and reduced response time even when the sample is positioned in a container having an annular projection at its bottom which is mounted on a rest or a heater plate and heated through the container while the rest or the heater plate is heated.

A sample heater for use in a microscope according to a first embodiment of the present invention comprises a rest for a microscope at least part of which is constructed as a heater, a first heater box forming a first space which surrounds a culture observation container mounted on the upper surface of the heater position of the rest, a second heater box forming a second space which surrounds the first heater box together with the first heater box, and heater means for heating the second space.

In a preferred embodiment the sample heater includes a temperature controller for providing temperature feedback control through which the temperature of the heater of the rest is fed back to be compared to a preset temperature.

A sample heater according to a second embodiment of the present invention comprises a temperature controller which previously stores correlation data between a first temperature at a first position in the vicinity of the sample mounted on the rest and a second temperature at a second position. The second position is affected by the temperature from the sample and a first temperature sensor for detecting the second temperature is also provided. Thus the controller controls the temperature of the sample, and particularly the temperature of a heater means so as to control the part of the sample to be at a preset temperature. This is made possible by correlating data from output signals from the first temperature sensor.

It is preferred that the sample heater includes a second temperature sensor for detecting the ambient temperature of the microscope at a third position which is different from the first and second positions, whereby the controller controls the heater means based on the correlation of data in response to output signals from the first and second sensors.

A sample heater according to a third embodiment of the present invention is removably attached to a rest platform of a microscope and comprises an inter-seat having a through-hole for observation, a heater means for heating the inter-seat, a temperature sensor for detecting a surface temperature of the inter-seat and a temperature controller for providing feedback control of the heater means by comparing a temperature detected by the temperature sensor with a preset temperature.

A sample heater according to a fourth embodiment of the present invention comprises a transparent electrode having electric resistance located on the surface of a culture observation container the electrode heats the sample and is itself heated through a current from a power supply which passes through the electrode.

A sample heater according to a fifth embodiment of the present invention comprises a rest for a microscope at least part of which is directly or indirectly heated and a plate seat having a through-hole for observing the sample. The plate seat has a configuration adapted to fit into the inside of an annular projection provided on the bottom of a culture observation container which is mounted on the upper surface of the rest so as to be interposed between the container and the rest while being fitted into the inside of the annular projection of the container.

According to the present invention, since a sample is directly heated by the rest platform the response time is reduced. Since a space surrounding the sample is closed dust does not harmfully enter the circumference of the sample and the inside of the heater box does not become dusty, so that no dust sticks to the sample and the inner surface of the first heater box is not clouded. Since the heater box is on the upper surface of the rest, the conversion of a revolver for an objective lens and operation of a compensating ring of an objective lens are not disturbed. In addition, even when an observation position is changed a reagent can be reliably injected into the observation position. A wide area of observation can be obtained by changing the relative position between the sample and the rest. As a result, the injection of a reagent and the positional adjustment of a cultured sample can be performed without uncovering a lid of the heater box and therefore the $CO_2$ concentration within the heater box does not change. Further, heated air does not leak out and dust cannot enter into the box. The heater box can remain stationary even when the rest is moved, so that a heater cord need not be pulled and the field of observation is not inadvertently moved. The second space is heated by the heater and no harmful vibration occurs.

Further, according to the present invention, correlation data between a first temperature at a first position in the vicinity of the sample placed on the rest and a second temperature at a second position which is different from the first position but is affected by the temperature at the part of the sample are stored in advance. Thus, the temperature sensor has no effect on the sample located on the rest and therefore the sample can be accurately and effectively heated to a preset temperature.

Still further, according to the present invention, the sample heater comprises an inter-seat which can be removed from the rest platform, a heater means for heating the inter-seat, a temperature sensor for detecting a surface temperature of the inter-seat and a temperature controller for providing feedback control of the heater means by comparing the temperature detected by the temperature sensor with a preset temperature. In addition, the upper surface of the inter-seat is even with the upper surface of the rest and therefore the whole surface of the rest is flat so that even a large size observation container can be placed on the rest in a stable fashion. Since the observation position or the in-focus position of the sample is not raised, even an objective lens of the high magnification whose operational distance is reduced can be used as before. The inter-seat, being removable, can be built in the sample heater as necessary.

A pair of connectors which are coupled to each other while the inter-seat is mounted on the rest are provided on the rest and the inter-seat, respectively, so that electric connection between the inter-seat and the rest platform is significantly facilitated. The relative positions of the connection is such that the connectors are automatically connected when the inter-seat is placed on the rest. When a ceramic heater or a sheet heater is used, the manufacturing cost can be reduced and the watertightness can be improved. Also, the temperature sensor can be built in the sample heater, resulting in a simple construction. When the resistance pattern in the vicinity of a through-hole for the observation has a higher density than that in the circumference thereof, the heat value in the vicinity of the through-hole increases so that the temperature drop in the vicinity of the field of observation of the observation container due to the heat losses is compensated. In addition, with an observation container having projection at its bottom, when a groove having a configuration corresponding to that of the projection of the container is provided on the upper surface of the inter-seat, almost the entire bottom surface of the container abuts the upper surface of the inter-seat so that the container can be effectively heated through the inter-seat in uniform fashion.

When the peripheral side of the inter-seat is formed such that the surface area thereof in contact with the inner peripheral plane of the rest is reduced, the heat conduction from the inter-seat to the rest is obstructed and therefore the thermal efficiency is improved. Further, a restrainer with a through-hole in alignment with the through-hole for the observation of the inter-seat is fixed to the inter-seat. The restrainer holds the observation container mounted on the upper surface of the inter-seat and heats the observation container, so that the observation container is heated from the upper and lower surfaces thereof. As a result, the response time to a preset temperature is further reduced and waterdrops produced on the upper inner surface of the observation container due to the temperature difference between the inside and outside air do not adhere thereto, resulting in the good observation, especially with a phase contrast microscope.

According to the present invention, since a transparent electrode is provided on the surface of the culture observation container to generate heat when a current is passed therethrough, the container is directly and effectively heated and the temperature control is easily achieved. Accordingly, the sample heater can produce any desired temperature distribution and is still simple and compact in construction.

Further, according to the present invention, a plate seat can be interposed between the culture observation container with the annular projection on its bottom and the rest so as to eliminate the air layer between the container and the rest. As a result, the temperature distribution in the container is uniform and thus a sample within the container can be properly heated, resulting in the high thermal efficiency and further reduced response time.

BRIEF DESCRIPTION OF THE DRAWINGS

FIG. 16 is a section view of the essential parts of a modification of the inter-seat shown in FIG. 8 which is in use;

DESCRIPTION OF THE PREFERRED EMBODIMENTS

Figure 1:
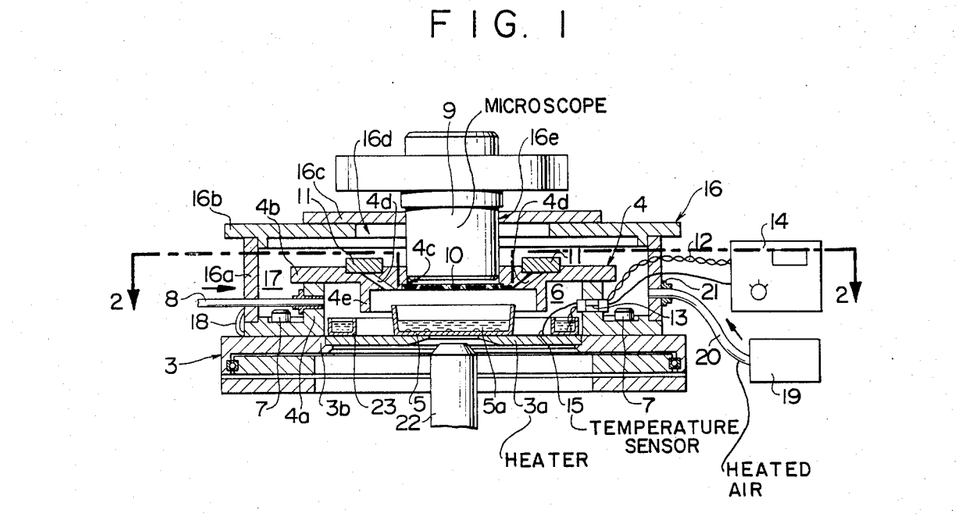
FIG. 1 is a vertical section view of a sample heater for use in microscopes according to a first embodiment of the present invention.

Referring now to FIG. 1, a rest or platform 3 for an inverted type microscope includes an inter-seat 3a which is also a heater and a support 3b to which the inter-seat 3a is removably attached and which is movable in a direction perpendicular to the plane of the figure. A first heater box 4 of airtight construction forms a first space 6 which surrounds a culture observation container 5 containing a sample 5a and mounted on the upper surface of the inter-seat 3a comprises a peripheral wall 4a which is fixed to the upper surface of the support 3b by means of screws 7 and a lid 4b. The peripheral wall 4a is provided with a through-hole for passages therethrough of a tube 8 which can be used for passing a gas such as $CO_2$ to the space 6 when necessary in accordance with a particular application.

The lid 4b includes a through-hole 4c into which the front end of a lens barrel of a condenser lens 9 of the microscope is fitted and whose bottom end is blocked by a transparent member 10. A plurality of through-holes 4d (four in the embodiment) for entry therethrough of a reagent or insertion of a temperature sensor are also provided. A humidity sensor and the like which are opened and closed by respective lids 11 and a flange 4e are provided on the lower surface of the lid 4b and on the outer peripheral side of the through-holes 4d and surrounding the container 5. The lid 4b is slidable on the upper edge of the peripheral wall 4a in airtight manner.

A cord 12 for supplying power to the heater of the inter-seat 3a is connected through a connector 13 to a temperature controller 14. A temperature sensor 15 arranged on the upper surface of the inter-seat 3a is also connected to the temperature controller 14.

A second airtight heater box 16 which forms a second space 17 surrounding the first heater box 4 together with the first heater box 4 includes a peripheral wall 16a which is fixed to the upper surface of the support 3b by being attached to the outer edge of the first heater box 4 by a clamp 18. A lid 16b is fixed to the peripheral wall 16a and has a centrally located and sufficiently large hole 16d as compared to the diameter of a barrel of the condenser lens 9. It also has a slide member 16c slidably mounted on the lid 16b and having a central through-hole 16e into which the condenser lens is closely fitted. The peripheral wall 16a has a hole 21 for passage therethrough of a tube 20, as shown in FIG. 1, which is connected to a fan 19 which supplies heated air to the second space 17. Reference numerals 22 and 23 represent an objective lens of an inverted type microscope and an annular water vessel, respectively.

In operation, the culture observation container 5 containing a culture sample 5a is first mounted on the inter-seat 3a which also is a heater. When the sample 5a requires humidity a water vessel 23 filled with water is similarly mounted on the inter-seat 3a. Subsequently, a predetermined temperature is set by the temperature controller 14 and power is supplied to the inter-seat 3a. The culture observation container 5 is directly heated as the inter-seat 3a generates heat and air in the first space 6 is heated by the natural convection of heat.

In the meanwhile, heated air is blown from the heated air fan 19 through the tube 20 into the second space 17 to thereby heat it. Thus, the first heater box 4 is heated until its inner surface temperature is higher than the air temperature in the first space 6 so that the water vapor emitted from the water vessel 23 or the sample 5a is not condensed on the inner surface of the first heater box 4.

Figure 3:
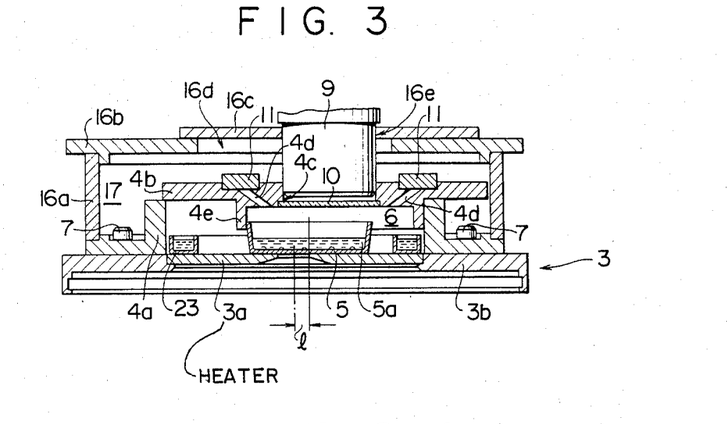
FIG. 3 is a vertical section view of the sample heater in FIG. 1 which is in operation.

The condenser lens 9 is fitted into the through-hole 4c of the lid 4b and when the rest 3 is moved, as shown in FIG. 3, the lid 4b slides on the peripheral wall 4a which moves together with the rest 3, so that the lid 4b remains stationary relative to the microscope. Accordingly, the through-holes 4d provided in the lid 4b remain in their relative position with respect to the focus on the optical axis. Even when the rest 3 moves a reagent or the like can be reliably injected toward the position which is being observed. It is to be noted, however, that the through-hole 4d may be formed along a different direction, if necessary. In addition, when the rest 3 moves to its limit, as shown in FIG. 3, the container 5 abuts against the flange 4e. Assuming that the range of movement of the container 5 is and the hole diameter of the inter-seat 3a is A, the observation range of the sample 5a is represented by A+2.

Figure 2:
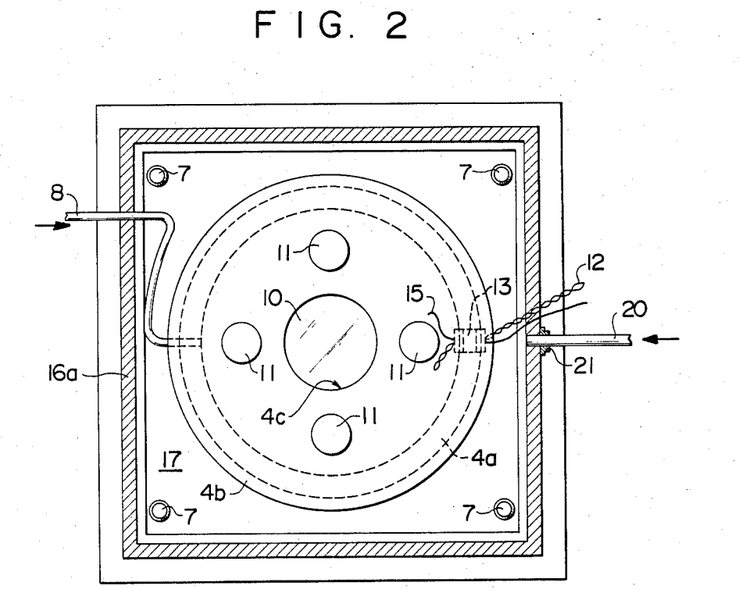
FIG. 2 is a horizontal section view of the sample heater shown in FIG. 1.
Figure 4:
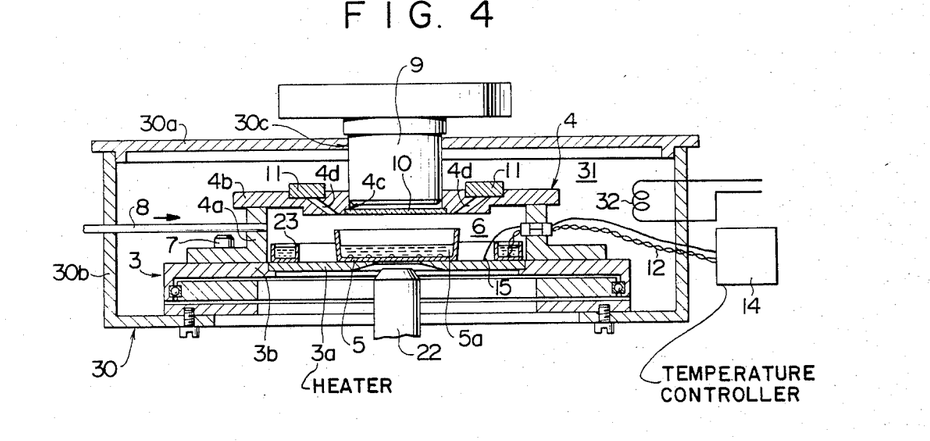
FIG. 4 is a vertical section view illustrating a modification of the sample heater shown in FIG. 1.

FIG. 4 illustrates a modification of the sample heater shown in FIGS. 1 to 3, wherein like reference characters designate like members in the sample heater shown in FIGS. 1 to 3. Therefore a detailed description of these elements is omitted. A second heater box 30 which is fixed to the lower side of the rest 3 by means of screws, has a lid 30a, a peripheral wall 30b to which the lid 30a is fixed and a center hole 30c into which the condenser lens 9 is fitted. A heater 32 is arranged in a second space 31 which is formed between the first heater box 4 and the second heater box 30. The second space 31 is heated by the heater 32 in a manner similar to the second space 17 of the first embodiment shown in FIGS. 1 to 3.

Figure 5:
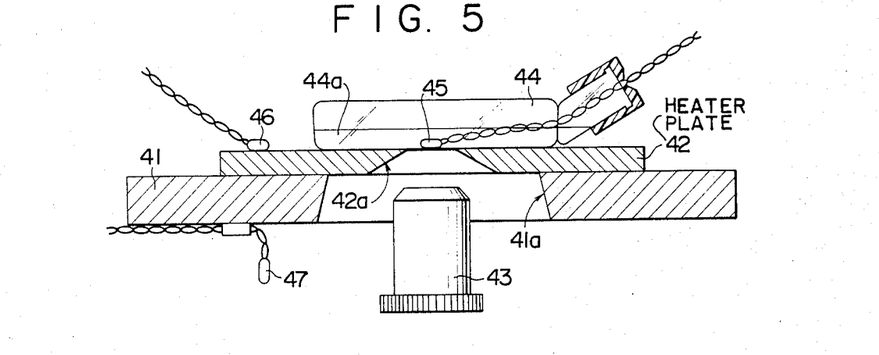
FIG. 5 is a section view of the essential parts of a sample heater for use in microscope according to a second embodiment of the present invention.

In FIG. 5, which illustrates a sample heater according to a second embodiment of the present invention, a heater plate 42 is arranged on the upper surface of a rest 41 of an inverted type microscope, which plate is constructed as part of the rest 41 or is fixed thereto. The heater plate 42 has a through-hole 42a which communicates with a through-hole 41a which is provided in the rest 41 and has a diameter which allows an objective lens 43 of a microscope to be inserted thereinto. A culture observation container 44 is mounted on the heater plate 42. A reference temperature sensor 45 which detects a temperature at a position in the vicinity of the portion of the sample 44a under observation (hereinafter referred to as a first position) is arranged within the container 44. A first correlation temperature sensor 46 is arranged at a second position (on the upper surface of the heater plate 42 in this embodiment) which is different from the first position and is affected by the temperature at the sample 44a i.e., the temperature detected by the reference temperature sensor 45.

In addition, a second correlation temperature sensor 47 is arranged at a third position, for example, a position which is not affected by the temperature at the observing portion of the sample 44a (under the rest 41 in this embodiment).

Figure 6:
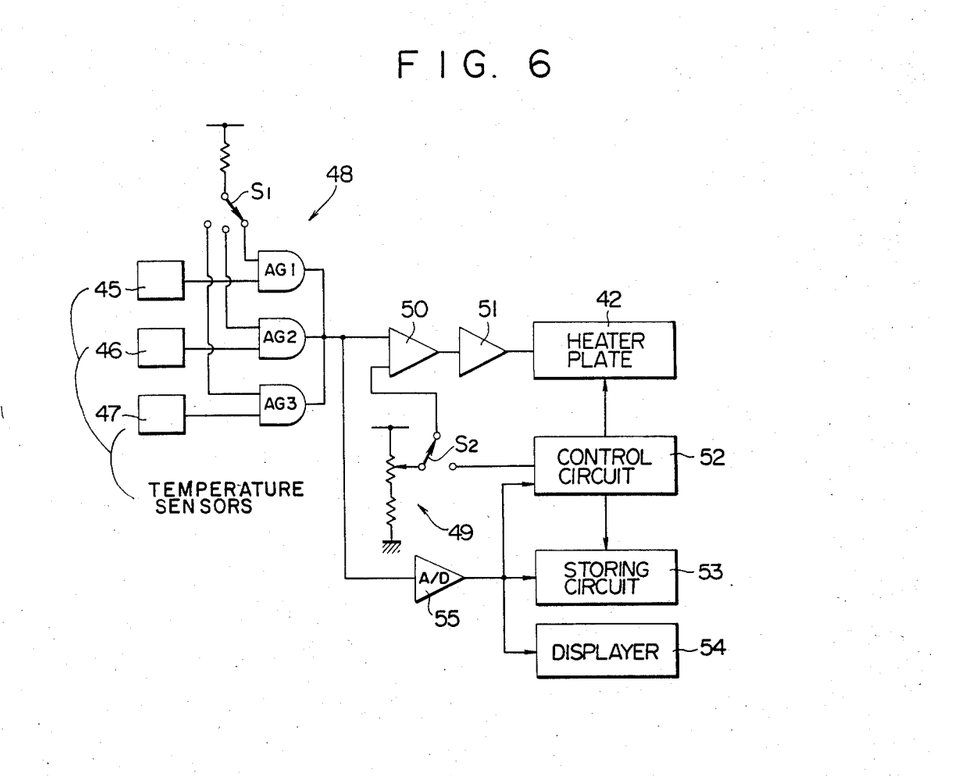
FIG. 6 is a block diagram of the sample heater shown in FIG. 5.

The temperature sensors 45, 46 and 47, as shown in FIGS. 6, have output terminals connected to input terminals of analog switches $AG^1$, $AG^2$ and $AG^3$, respectively. Input terminals for control signals of the analog switches $AG^1$, $AG^2$ and $AG^3$ are connected to first, second and third fixed contacts of a first changeover switch $S_1$ the switch $S_1$ constitutes a selection circuit 48 together with the analog switches $AG^1$, AG2 and AG3, respectively. A high level voltage is applied through a resistor to a contact terminal of the switch $S_1$. Output terminals of the analog switches AG1, AG2 and AG3 are connected all together to one of input terminals of a comparator 50 and to an input terminal of an A/D converter 55. A variable resistor 49 serving as a temperature setting circuit is connected through a changeover switch $S_2$ to the other input terminal of the comparator 50. One end of the variable resistor 49 is grounded and a high level voltage is applied to the other end thereof. A movable contact terminal of the variable resistor 49 is connected to a contact terminal of the switch $S_2$. One fixed contact terminal of the switch $S_2$ is connected to the other input terminal of the comparator 50 and the other fixed contact terminal thereof is connected to a control circuit 52. An output terminal of the comparator 50 is connected through an amplifier 51 to the heater plate 42. An output terminal of the A/D converter 55 is connected to an indicator 54 for indicating temperature detected by each of the temperature sensors 45, 46 and 47. The control circuit 52 is connected to both the heater plate 42 and a storage circuit 53.

In operation, an initial temperature setting is made at the temperature control. As shown in FIG. 5, the culture observation container 44 containing the sample 44a is mounted on the heater plate 42 of the rest 41. Specifically, before actual observations are begun the reference temperature sensor 45 is positioned at the first position or at a position in the vicinity of the container 44. Then correlation data between a first temperature at the first position and a second temperature at the second position are recorded. Firstly, the switch $S_1$ in the selection circuit 48 is changed such that an output of the reference temperature sensor 45 is applied to one input terminal of the comparator 50 and the switch $S_2$ is switched to the comparator 50 so that a temperature of the heater plate 42 is controlled with the comparator 50 which presets the temperature with the end of variable resistor 49. When it is confirmed, by indicator 54, that the first temperature as measured by sensor 45 has reached the preset temperature, the first temperature is stored in the storing circuit 53. Subsequently, the switch $S_1$ is changed to the first correlation temperature sensor 46. Then, the second temperature detected by the sensor 46 is displaced on the indicator 54 and is inputted into the storing circuit 53. The correlation data between the first preset temperature and the second temperature are stored in the storing circuit 53. It will be understood that with change of a preset temperature correlation data between first and second temperatures are stored in the storage circuit 53.

In the sample heater in which the initial temperature setting has been completed as described above, operations for observing the sample 44a which is heated below the microscope will be described. At this time, the reference temperature sensor 45 is removed from the container 44 and the sample to be observed is placed therein. In addition, the switch $S_1$ is through to the first correlation temperature sensor 46 side and the switch $S_2$ is positioned to the control circuit 52 side. The variable resistor 49 is set at a predetermined temperature which is monitored. This is a position corresponding to the first temperature and therefore a voltage corresponding to the position set by the resistor 49 is produced. A second temperature corresponding to the preset temperature is produced by an A/D converter circuit (not shown) in the control circuit 52, from digital value previously stored there. The second temperature is compared with an output from the A/D converter 55 in a comparator (not shown). The compared output is applied to the heater plate 42 to set the temperature at the second position on the heater plate 42 to the second previously obtained preset temperature so that a temperature at the first position or the position in the vicinity of observing portion of the sample 44a is correctly controlled. It is to be noted that when an equal quantity of the same culture is observed in the same container the temperature control is precise and same temperature setting can be obtained repeatedly with the correlation data previously stored without rearrangeing the reference temperature sensor 45.

It should be also noted that when first and second temperatures detected by respective sensore 45, 46 are controlled based on temperature deviation from an ambient temperature of the microscope as detected by the second correlation temperature sensor 47, a more precise temperature control is achieved. With the above method the controller is affected also by the ambient temperature.

Figure 7:
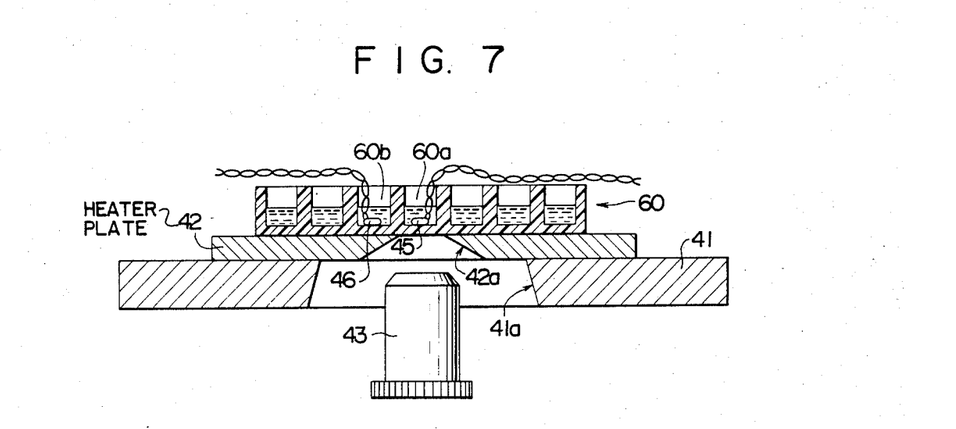
FIG. 7 is a section view of the essential parts of a modification of the sample heater shown in FIG. 5.

In FIG. 7, which illustrates an arrangement in which a microtest plate 60 is used as a culture observation container, the reference temperature sensor 45 is arranged within a cell 60a which is located at an observing position of the microtest plate 60. The first correlation temperature sensor 46 is arranged within a cell 60b other than the cell 60a (a cell next to the cell 60a in FIG. 7) and its temperature control is the same as that in the embodiment shown in FIGS. 5 and 6.

While the foregoing embodiments relate to the structure in which the heater plate is provided on part of the rest of the microscope, the present invention can also be applied to a sample heater in which a heater chamber is formed on the upper surface of a rest to heat air within the heater chamber as a sample control device which includes a cooler means in place of the heater means described above. Samples to be observed are not limited to cultured cells and may be germs, metallic samples or the like. A temperature sensor may be arranged at any position. Further, a plurality of temperature sensors are arranged so as to achieve a divisional control of a heater, whereby the temperature distribution within the observation field can be optionally controlled. The electric circuit shown in FIG. 6 is only an example and other circuits may be employed. In particular, when a microcomputer is incorporated, it is possible to obtain complicated program control.

Figure 8:
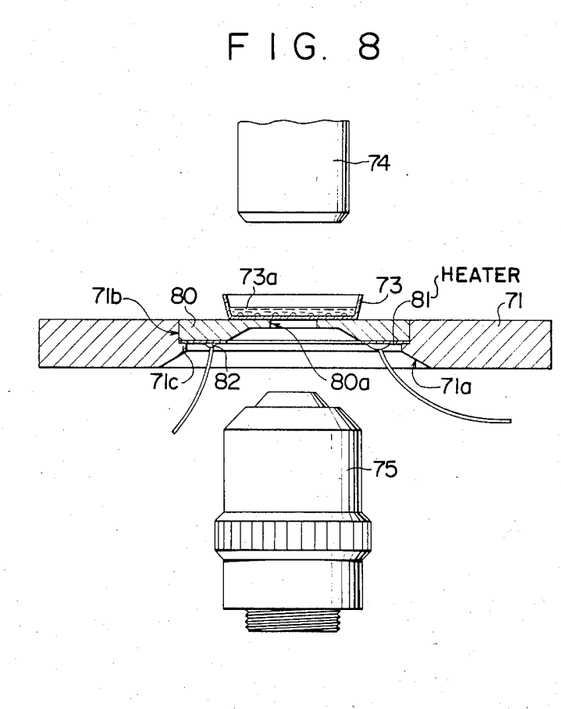
FIG. 8 is a section view of the essential parts of a sample heater for use in microscopes according to a third embodiment of the present invention.

In FIG. 8, which illustrates a sample heater according to a third embodiment of the present invention, a rest 71 of an inverted type microscope has a hole 71b in its upper side and a step 71c. It communicates with a hole 71a provided for the observation of a sample and having the diameter of an objective lens 75 which can be inserted thereinto. An inter-seat 80 having substantially the same outside diameter as the inside diameter of the hole 71b is removably fitted into the hole 71b in such a manner that the lower peripheral edge of the inter-seat 80 abuts against the step 71c and the upper surface thereof is substantially even with the upper surface of the rest 71. The inter-seat 80 has an observation through-hole 80a substantially in its center part and a heater 81 for heating the inter-seat 80 such as a sheet heater which is attached to a portion thereof so as not to hinder the observation field on the back of the inter-seat 80.

A temperature sensor 82 for detecting a surface temperature such as a nichrome sensor and a platinum sensor is attached to the inter-seat 80. Reference numerals 73, 73a and 74 represent a culture observation container, a sample contained within the container 73 and a condenser lens, respectively.

Figure 9:
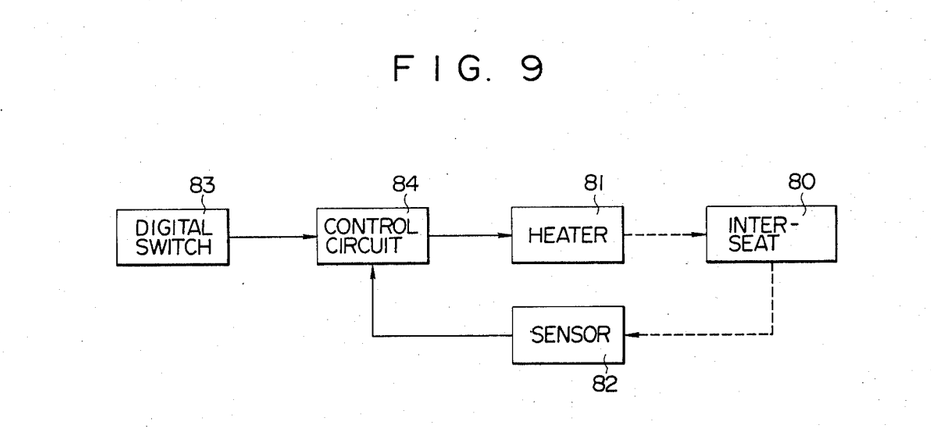
FIG. 9 is a block diagram of an electric circuit of the sample heater shown in FIG. 8.

FIG. 9 illustrates an example of a temperature controller of the heater 81. A control circuit 84 is connected to both a digital switch 83 and the sensor 82 for manually setting a temperature. The control circuit 84 compares the surface temperature of the inter-seat 80 which is detected by the temperature sensor 82 with a temperature preset by the digital switch 83 to control a current to the heater 81, thus a temperature of the inter-seat 80 being controlled by feedback control. It will be understood that a construction of electric circuit other than the foregoing circuit may be employed.

In operation, a predetermined temperature such as the optimum temperature for studying a cultured cell (for example, 37C) is first set by the digital switch 83 and the control circuit 84 supplies a current to the heater 81 to heat the inter-seat 80. Comparing the surface temperature of the inter-seat 80 detected by the sensor 82 with the temperature preset by the digital switch 83, the current to the heater 81 is controlled by the feedback control or the on-off control based on the temperature difference to keep the inter-seat 80 at the predetermined temperature. At this time, the upper plane of the inter-seat 80 is even with the upper plane of the rest 71 and the rest 71 has no projection and is completely flat so that even when a large size observation container is used the container rests stably thereon. The observation position or the focusing position of the sample 73a is not raised so that even an objective lens of the high magnification which has a reduced operational range can be used as in the past. In addition, the inter-seat 80 is removable from the rest 71 so that the inter-seat 80 in which the heater 81 and the temperature sensor 82 are built can be positioned on the rest 80 only when necessary. Also, the heater 81 and the temperature sensor 82 can be built in the inter-seat 80 afterward.

Figure 10:
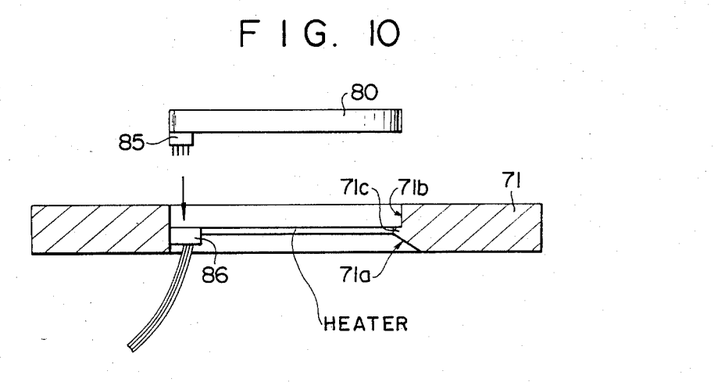
FIG. 10 is a section view of the essential parts of a modification of the sample heater shown in FIG. 8.

In the modified sample heater shown in FIG. 10, the rest 71 and the inter-seat 80 have a pair of connectors 85, 86, respectively, which serve to connect power supply lines to a heater means as well as for temperature sensors signal lines and are automatically coupled to each other when the inter-seat 80 is mounted on the rest 71. Thus, the inter-seat 80 can be easily mounted and removed.

Figure 11:
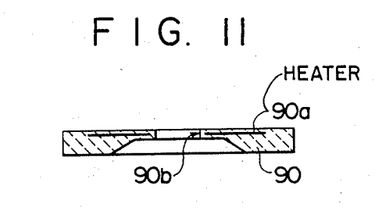
FIGS. 11 and 12 are vertical and horizontal section views illustrating another example of an inter-seat shown in FIG. 8.
Figure 12:
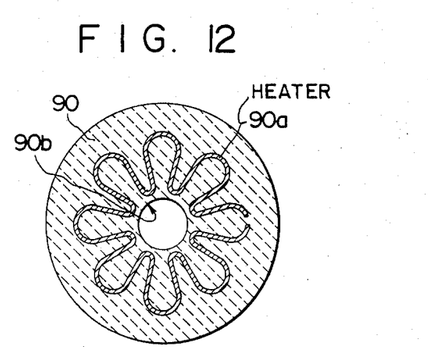

FIG. 11 illustrates an arrangement in which both an inter-seat 90 and a heater are integrated as a ceramic heater. For example, the arrangement is formed by a resistor pattern 90a as shown in FIG. 12 or of any other configuration printed on one side of alumina ceramics which forms the inter-seat body and after an alumina insulating protector layer is coated thereon the sintering process is applied to the entirety of the device at a high temperature. With the resistor pattern 90a shown in FIG. 12, the pattern density around a through-hole 90b is higher than that of the periphery so that the heat value in the vicinity of the hole 90b increases to compensate for the temperature fall in the vicinity of the observation field due to rise of heat in the vicinity of the hole 90b.

Figure 13:
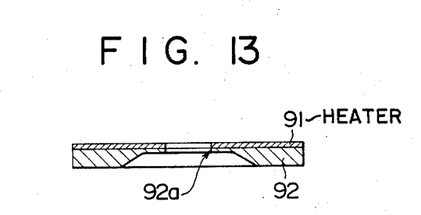
FIG. 13 is a section view illustrating a further example of the inter-seat shown in FIG. 8.

FIG. 13 illustrates a structure in which a sheet heater 91 which is sandwiched between metallic plates is attached as a heater means to the upper plane of an inter-seat 92 having a through-hole 92a for the observation. The sheet heater 91 is laminated in entirety with insulator layers such as silicone rubber and heat-resisting films and includes a resistor pattern of the configuration as shown in FIG. 12 or of other patterns and a temperature sensor, when as required. The structures shown in FIGS. 11 and 13 reduce manufacturing cost and have good water repelling properties.

Figure 14:
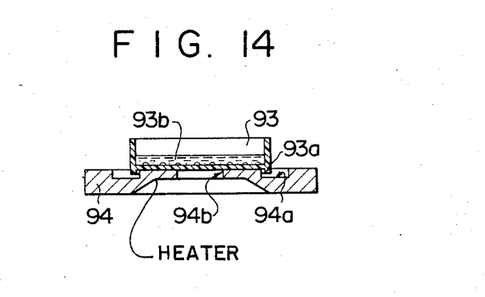
FIG. 14 is a section view of the essential parts of a still further example of the inter-seat shown in FIG. 8 which is in use.

FIG. 14 illustrates an inter-seat 94 having an observation through-hole 94b and which is adapted to be used for an observation container 93 such as a laboratory dish made of plastics having an annular projection 93a on its bottom for preventing damage thereto. The inter-seat 94 has a groove 94a of a shape corresponding to the annular projection 93a of the bottom of the container 93, on the upper surface. Accordingly, when the container 93 is mounted on the inter-seat 94 the annular projection 93a enters the groove 94a and the bottom of the container 93 abuts against the upper surface of the inter-seat 94. Thus, the container 93 is favorably heated through the inter-seat 94 in a uniform temperature distribution. When several types of observation containers are used corresponding inter-seats 94 having a groove of a respectively similar shape can also be used. Or at least one inter-seat having a plurality of grooves corresponding to all kinds of containers may be provided.

Figure 15:
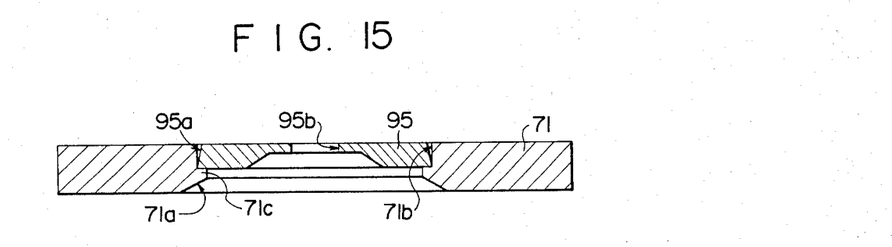

FIG. 15 illustrates an inter-seat 95 having an observation through-hole 95b whose peripheral side is sloped. Therefore, the contact surface between the inter-seat 95 and the rest 71 is reduced. For example, as shown in FIG. 15, the peripheral side of the inter-seat 95 has a slope 95a in the shape of a truncated cone tapering toward the upper part of the optical axis. With this structure, the heat loss due to the thermal conduction from the inter-seat 95 heated by a heater means to the rest 71 is greatly reduced.

Figures 16, 17:
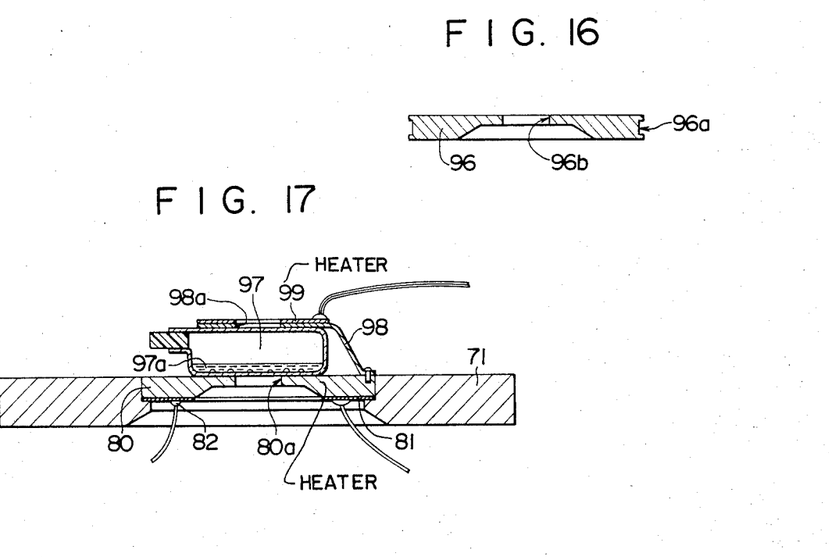
FIG. 16 is a section view illustrating another modification of the inter-seat shown in FIG. 8.
FIG. 17 is a section view of the essential parts of a modification in which a restrainer means is provided on the inter-seat shown in FIG. 8.

In FIG. 16, modification of the inter-seat shown in FIG. 15 is illustrated. The peripheral side of the inter-seat 95 with its observation through-hole 96b has an annular recess or a peripheral groove 96a leaving the upper and lower edge portions.

FIG. 17 illustrates restrainer 98 made of resilient material fixed to the inter-seat 80a. The restrainer 98 is a stainless sheet which holds the observation container 97 containing a sample 97a. The restrainer 98 includes a heater means 99 such as a sheet heater for heating the container 97 and a through-hole 98a in alignment with the hole 80a of the inter-seat 80. With this structure, the container 97 is heated from two opposite sides through the inter-seat 80 and the heater means 99. As a result, the container 97 can be rapidly heated to a preset temperature and the formation of waterdrops on the upper inner plane of the container 97 due to the temperature difference from the atmospheric temperature is prevented and if formed is prevented from sticking to the walls, which might otherwise reduce visibility in the container.

Figure 18:
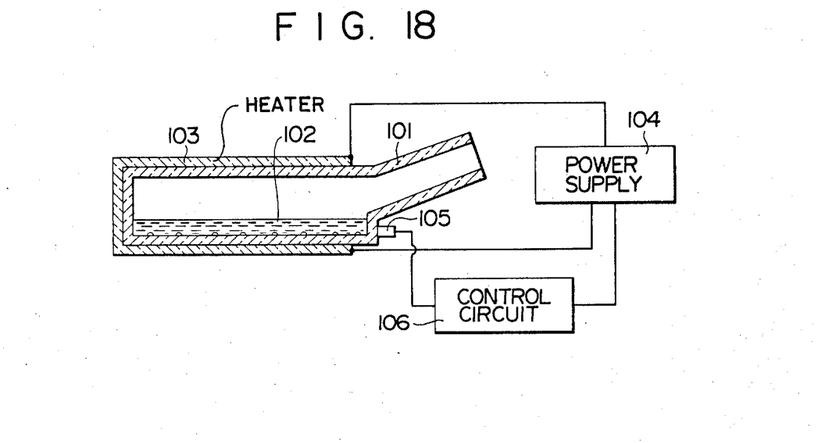
FIG. 18 is a section view of a sample heater for use in microscopes according to a fourth embodiment of the present invention.

FIG. 18 illustrates a sample heater for use in a microscope according to a fourth embodiment of the present invention. The sample heater comprises a culture observation container 101 made of transparent material and containing: a culture sample 102, a transparent and heater 103 formed on the surface of the container 101 by an evaporation process for example, a power supply 104 for supplying current to the heater 103, a temperature sensor 105 for detecting a temperature of the sample 102 or the container 101 and a control circuit 106 which controls a current from the power supply 104 to the heater 103 based on an output of the temperature sensor 105.

With the sample heater described above, when a current is supplied from the power supply 104 to the heater 103, the container 101 and the sample 102 are heated by the heater 103. A temperature of the sample 102 or the container 101 is detected by the temperature sensor 105. A current from the power supply 104 to the heater 103 is fed back and controlled by the control circuit 106. Thus, the temperature of the sample 102 or the container 101 is kept constant.

Figure 19:
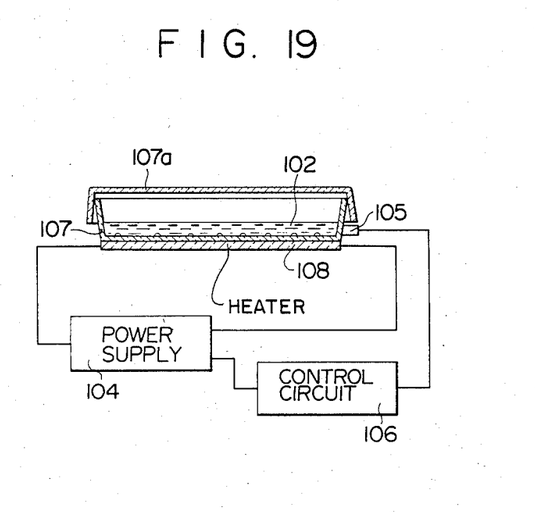
FIGS. 19 and 20 are section views of modifications of the sample heater shown in FIG. 18, respectively.
Figure 20:
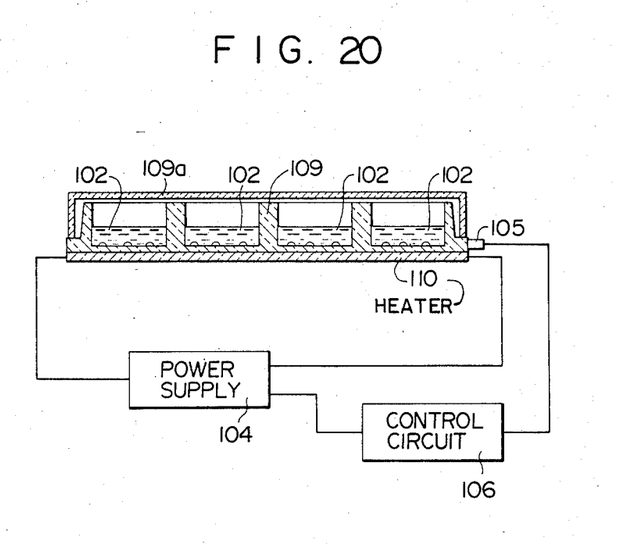

FIG. 19 illustrates a structure in which a transparent heater 108 having electrical resistance is formed on the bottom lower plane of a culture observation container 107 in the laboratory dish from having a lid 107a. FIG. 20 illustrates a structute in which a transparent heater 110 is formed on the bottom lower plane of a culture observation container 108 made of a microtest plate and having a lid 109a.

With the sample heaters constructed as shown in FIGS. 19 and 20, a sample 102 is heated in a manner similar to the sample heater shown in FIG. 18.

Figure 21:
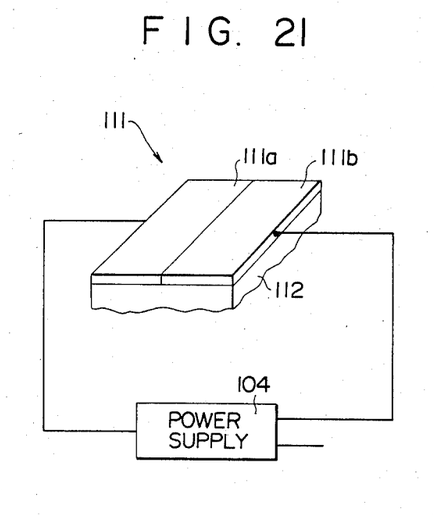
FIGS. 21 and 22 are perspective views of the essential parts of modifications of a transparent electrodes shown in FIGS. 19 and 20, respectively.
Figure 22:
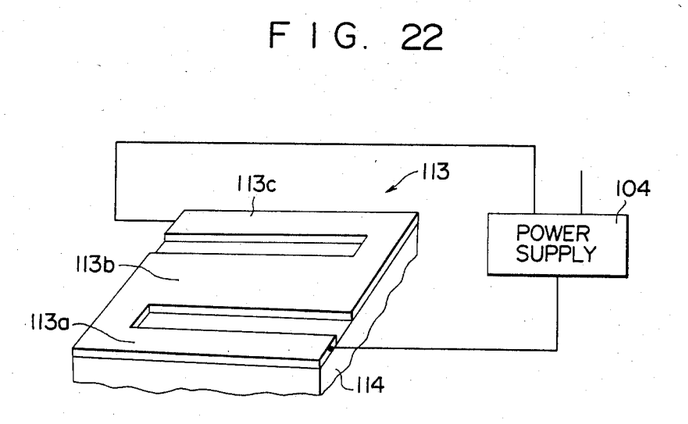

FIG. 21 illustrates a transparent heater 111 comprising transparent heater portions 111a and 111b which have different electric resistivities obtained by changing material thickness and the like. With this heater, a culture observation container 112 can be heated in a specific temperature distribution. FIG. 22 illustrates a transparent heater 113 comprising transparent heater portions 113a, 113b and 113c which have different electrical resistivities obtained by specific patterns and be partially changing the width of the heater portions. With this heater, a culture observation container 114 can be heated in accordance with a specific temperature distribution.

Figure 23:
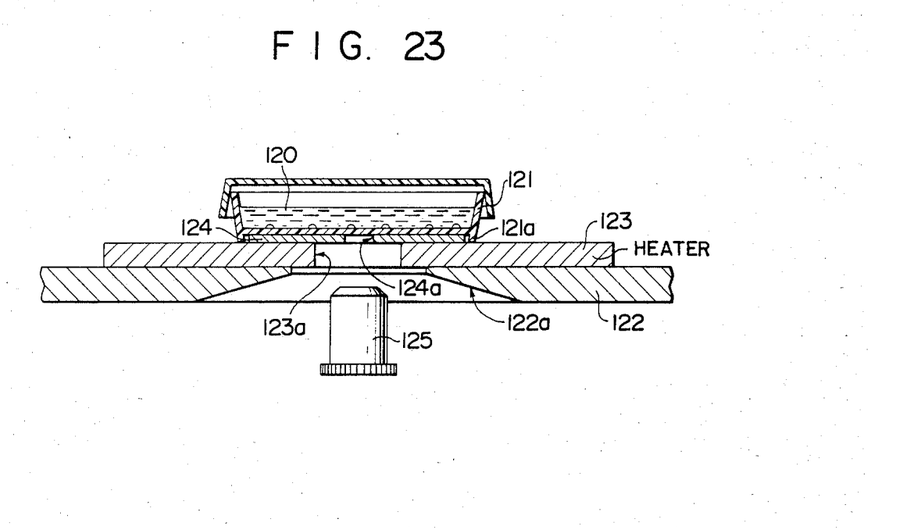
FIG. 23 is a section view of the essential parts of a sample heater for use in microscope according to a fifth embodiment of the present invention.
Figure 24:
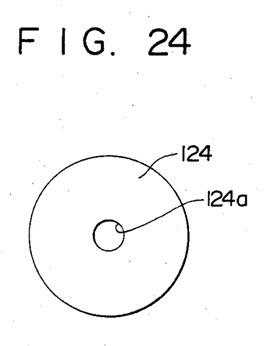
FIGS. 24 and 25 are plan views of a plate seat shown in FIG. 23 and its modification, respectively.

FIG. 23 illustrates a sample heater for use in a microscope according to a fifth embodiment of the present invention. A heater plate 123 with an observation through-hole 123a is constructed as part of a rest 122 for an inverted type microscope with an observation through-hole 122a. Alternately plate 123 is fixed to the rest 122. A culture container 121 of the laboratory dish type formed of plastics contains a sample 120 and has an annular projection 121a on the bottom thereof. A plate seat 124 made of material of the high thermal conductivity such as metals is interposed between the heater plate 123 and the container 121. The plate seat has a form which allows it to be inserted in the inside of the annular projection 121a and it also has an observation through-hole 124a (FIG. 24). The thickness of the plate seat 124 is chosen so as to be slightly larger than the height of the projection 121a so that the plate seat 124 is brought into contact all over the surface thereof with the bottom of the container 121. In addition, the hole 124a is selected to be larger than the observation field of the microscope and to be as reduced as possible in order to provide good thermal conductivity therethrough.

With the construction of the plate seat 124 as described above, when the container 121 is mounted through the plate seat 124 on the upper surface of the heater plate 123 so as to permit the plate seat 124 to be fitted into the inside of the annular projection 121a, the entire bottom surface of the container 121 is thermally in contact with the heater plate 123. Accordingly, the container 121 is well heated by thermal conduction from the heater plate 123, resulting in a uniform temperature distribution, high thermal efficiency and reduced response time. In addition, when the observation field changes by switching an objective lens 125, for example, plate seats having though-holes of different size and having the same configuration may be conveniently prepared. Then, a plate seat can be simply selected which is suitable for the observation field.

Figure 25:
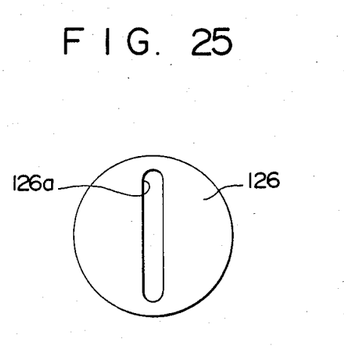

FIG. 25 illustrates a plate seat 126 which has a slot-shaped observation hole 126a. The container 121 and the plate seat 126 are moved relative to the heater plate 123 in the longitudinal direction of the hole 126a and only the container 121 is rotated relative to the plate seat 126 so that the container 121 can be observed substantially over its entire surface. In addition, since the area of the hole 126a is comparatively small, it is possible to maintain the thermal conduction in a good condition.

Figure 26:
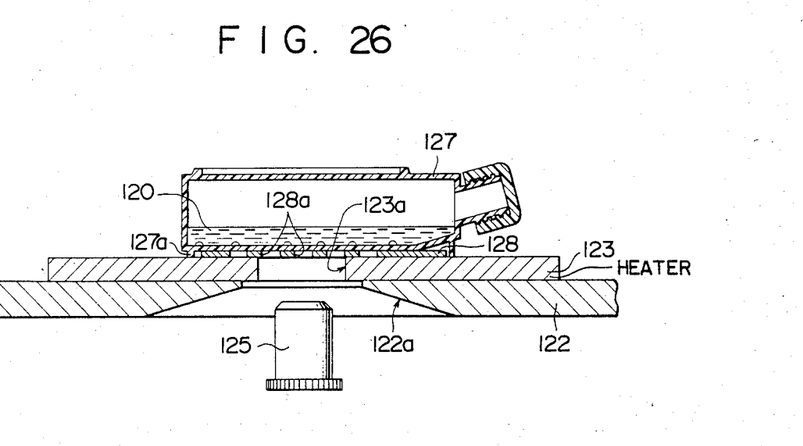
FIG. 26 is a section view of the essential parts of another example of the sample heater shown in FIG. 23.
Figure 27:
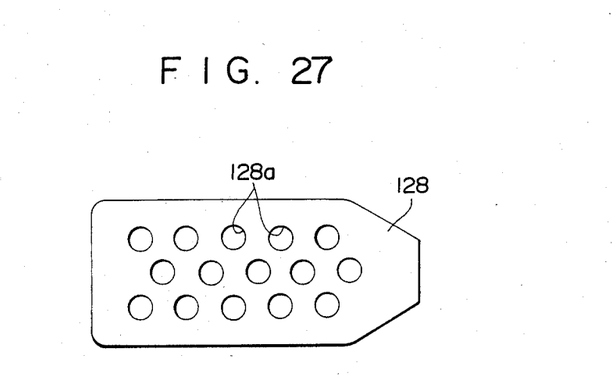
FIG. 27 is a plan view of a plate seat shown in FIG. 26.

FIG. 26 illustrates a culture observation container 127 of the flask type made of plastics which has an annular projection 127a along the outer peripheral edge of its bottom in a manner similar to the container 121 described above. A plate seat 128 (FIG. 27) is interposed between the container 127 and the heater plate 123. It has a configuration which allows it to be insertable into the inside of an annular projection 127a and a plurality of observation holes 128a so as to make various areas of the container 127 observable. The operation and effects of the plate seat 128 are similar to the plate seat 124 or 126 when used with the container 121 of the laboratory dish type.

The plate seat 124, 126, 128 can be made of metallic material such as aluminum, brass and stainless steel. In addition, the plate seat 124, 126 128 may be made of silicone rubber, for example, of high thermal conductivity. In this case, the observation through-hole can be easily provided in a silicone rubber sheet at a desired observation position by previously determining the position prior to heating and then cutting the sheet by scissors or the like according to the determined position.

In the foregoing description, a laboratory dish or flask is always shown to be mounted on the heater plate. However, even when the rest or platform of the microscope of the microscope itself is housed entirely in the heater box, the use of the plate seat is also effective. The reason is that the thermal conduction from the air heated rest to the observation container and to the sample is dominant as compared with the thermal conduction from heated air to the sample. In addition, the observation container is not limited to a laboratory dish or flask made of plastics as mentioned above but may have otherwise shaped projections on the bottom thereof.

What is claimed is:

1. A heater for a microscope, comprising:
   a platform for supporting thereon a sample container and means for heating at least part of the platform;
   a first heater box connected to said platform and forming a first space which surrounds said sample container;
   a second heater box, said first heater box being located in said second box and forming therewith a second space which surrounds said first heater box; and
   heater means for heating said second space.

2. A heater according to claim 1, wherein said platform is formed as part of said heater means and further including a temperature controller, said temperature controller including feedback control means for determining the temperature of said platform, for comparing said temperature to a preset temperature and for adjusting said temperature to said preset temperature.

3. A heater according to claim 1, in which said heater comprises a removable seat which is adapted to be mounted on said platform, said seat being adapted to support said sample container thereon.

4. A heater according to claim 1, in which said first space includes a water vessel mounted on said platform or supplying humidity to said first space to prevent drying of said sample.

5. A heater according to claim 1, in which said first heater box further includes conduit means for supplying therethrough a gas into said first space.

6. A heater as in claim 5 further comprising means for supplying a gas to said first space through said conduit means.

7. A heater according to claim 1, in which said first heater box includes through-hole means for injecting a reagent therethrough to a sample housed in said first space and for applying operation to said sample and a removable lid adapted to cover said through-hole means.

8. A heater according to claim 1, in which said first heater box includes a transparent surface which permits a sample located within said first space to be observed from outside said heater.

9. A sample heater according to claim 1, in which said heater means comprises an external heated air fan which communicates with said second space.

10. A heater according to claim 1, in which said means comprises a heater element located in said second space.

11. A sample heater for a microscope comprising:
    a seat for a sample container, the seat having a through-hole for observing a sample therethrough, said seat being removably positioned at an upper plane of a microscope platform, an upper surface of said seat being substantially even with said upper plane of said platform;
    heater means for heating said seat;
    a temperature sensor for detecting a surface temperature of said seat; and
    temperature feedback control means for comparing the temperature detected by said temperature sensor with a preset temperature and for controlling said heater means to heat said seat to a temperature which equals said preset temperature.

12. A heater according to claim 11, further including a pair of connectors coupled to said platform and said seat for interconnecting a power supply line to said heater means and a signal line to said temperature sensor, said connectors being coupled to each other when said seat is mounted on said platform.

13. A hater according to claim 11, in which said seat and said heater means are integrally constructed as a ceramic heater.

14. A heater according to claim 11, in which said heater means is formed as a sheet heater which is attached to said seat.

15. A heater according to claim 11, in which said heater means is adapted to provide more heat in the vicinity of said through-hole of said seat.

16. A heater according to claim 11, in which said seat includes a groove defined on the upper surface thereof, said groove having a configuration which is complementary to that of a projection defined on a bottom lower surface of a culture observation container which is to be mounted on said seat.

17. A heater according to claim 11, in which a peripheral surface of said seat which abuts said platform has a reduced thickness region whereby less heat passes from said seat to said platform.

18. A heater according to claim 11, further including a restrainer cantileverly fixed to said seat and projecting upwardly above said seat, said restrainer being adapted to hold a culture observation container placed on the upper surface of said seat against said seat, said restrainer including a through-hole which projects over the through-hole of said seat and heater means for heating said container.

19. A heater for a microscope comprising:
a sample holding container having an electrically resistant and transparent heater formed on at least one surface thereof;
means for supplying a current to said transparent heater;
a temperature sensor for detecting a temperature at a given position within said container; and
feedback control means for controlling said current to have a magnitude which produces a preset temperature at said given position.

20. A heater according to claim 19, in which said transparent heater comprises a plurality of transparent heater portions having different electric resistances.

21. A heater according to claim 19, in which said transparent heater is formed to produce a predefined temperature distribution over portions of said container.

22. A heater for a microscope comprising:
a platform for the microscope and means for heating said platform;
a container for holding a sample, and having an annular projection on a lower plane thereof adjacent said platform; and
a plate seat which fits within said annular projection and having a through-hole for observing said sample therethrough, said plate seat being interposed between said container and said platform to improve heat conduction between said platform and said container.

23. A sample heater for a microscope of the type in which the temperature of a sample placed in a sample container must be accurately controlled, said heater comprising:
a reference temperature sensor removably locatable at a first position in said sample container;
a first correlation temperature sensor located away from said container and at a second position;
storage means responsive to said reference sensor and said correlation sensor for measuring the temperature at said first and second positions and for developing and storing a correlation relationship between temperatures at said first and second positions; control means responsive to said correlation relationship of said storage means and to said first correlation temperature sensor which indicates the temperature at said second position to develop a control signal whenever it is determined, based on said temperature at said second position and on said correlation relationship, that the temperature at said first position deviates from a preset temperature; and
heater means responsive to said control signal for increasing the temperature at said first position to said preset temperature.

24. A heater according to claim 23, further including a second correlation temperature sensor at a third position which is different from said first and second positions, said second correlation temperature sensor being provided for sensing the ambient temperature of said microscope, said storage means developing said correlation relationship based additionally on an output from said second correlation temperature sensor.

* * * * *